United States Patent
Cinoglu et al.

(10) Patent No.: US 6,965,231 B1
(45) Date of Patent: Nov. 15, 2005

(54) BELT BUCKLE AND USE THEREOF IN MAGNETIC RESONANCE IMAGING

(75) Inventors: Arto Cinoglu, Oceanside, NY (US); Mark Gelbien, Levittown, NY (US); Joseph Citro, Hauppauge, NY (US)

(73) Assignee: Fonar Corporation, Melville, NY (US)

(*) Notice: Subject to any disclaimer, the term of this patent is extended or adjusted under 35 U.S.C. 154(b) by 0 days.

(21) Appl. No.: 10/698,119

(22) Filed: Oct. 31, 2003

(51) Int. Cl.[7] ................................................. G01V 3/00
(52) U.S. Cl. ...................................... 324/300; 324/307
(58) Field of Search ................................ 324/300, 307, 324/309, 311, 318, 319, 322

(56) References Cited

U.S. PATENT DOCUMENTS

| | | | |
|---|---|---|---|
| 3,381,268 A | * | 4/1968 | Boblitz ..................... 180/270 |
| 3,648,333 A | | 3/1972 | Stoffel |
| 3,649,999 A | | 3/1972 | Stoffel |
| 4,052,774 A | * | 10/1977 | Noda ..................... 24/587.12 |
| 4,150,464 A | * | 4/1979 | Tracy ......................... 24/313 |
| 4,317,263 A | | 3/1982 | Fohl |
| 4,393,556 A | * | 7/1983 | Yuda et al. .................. 24/662 |
| 4,991,272 A | * | 2/1991 | Bianchi ....................... 24/616 |
| 5,033,171 A | | 7/1991 | Kasai |
| 5,832,573 A | | 11/1998 | Howell |
| 5,970,587 A | | 10/1999 | Knox |
| 6,000,110 A | | 12/1999 | Wier |
| 6,023,165 A | * | 2/2000 | Damadian et al. .......... 324/318 |
| 6,079,744 A | | 6/2000 | Husby |
| 6,123,166 A | | 9/2000 | Verellen |
| 6,205,629 B1 | | 3/2001 | Becker |
| 6,357,091 B1 | | 3/2002 | Devereaux |
| 6,389,661 B1 | | 5/2002 | Brown et al. |
| 6,414,490 B1 | | 7/2002 | Damadian et al. |
| 6,677,753 B1 | | 1/2004 | Danby et al. |

* cited by examiner

Primary Examiner—Brij B. Shrivastav
(74) Attorney, Agent, or Firm—Lerner, David, Littenberg, Krumholz & Mentlik, LLP

(57) ABSTRACT

In an embodiment, a belt buckle comprises a housing and locking member that are secured by a pair of locking levers. The housing includes the locking levers along with a base plate to which the locking levers are individually mounted in association with a spring bias. In another embodiment, a belt buckle comprises a housing, a locking member and an optical switch that provides and indication of when the locking member is secured to the housing. In another aspect of the invention, the buckle assemblies are magnetically translucent.

18 Claims, 14 Drawing Sheets

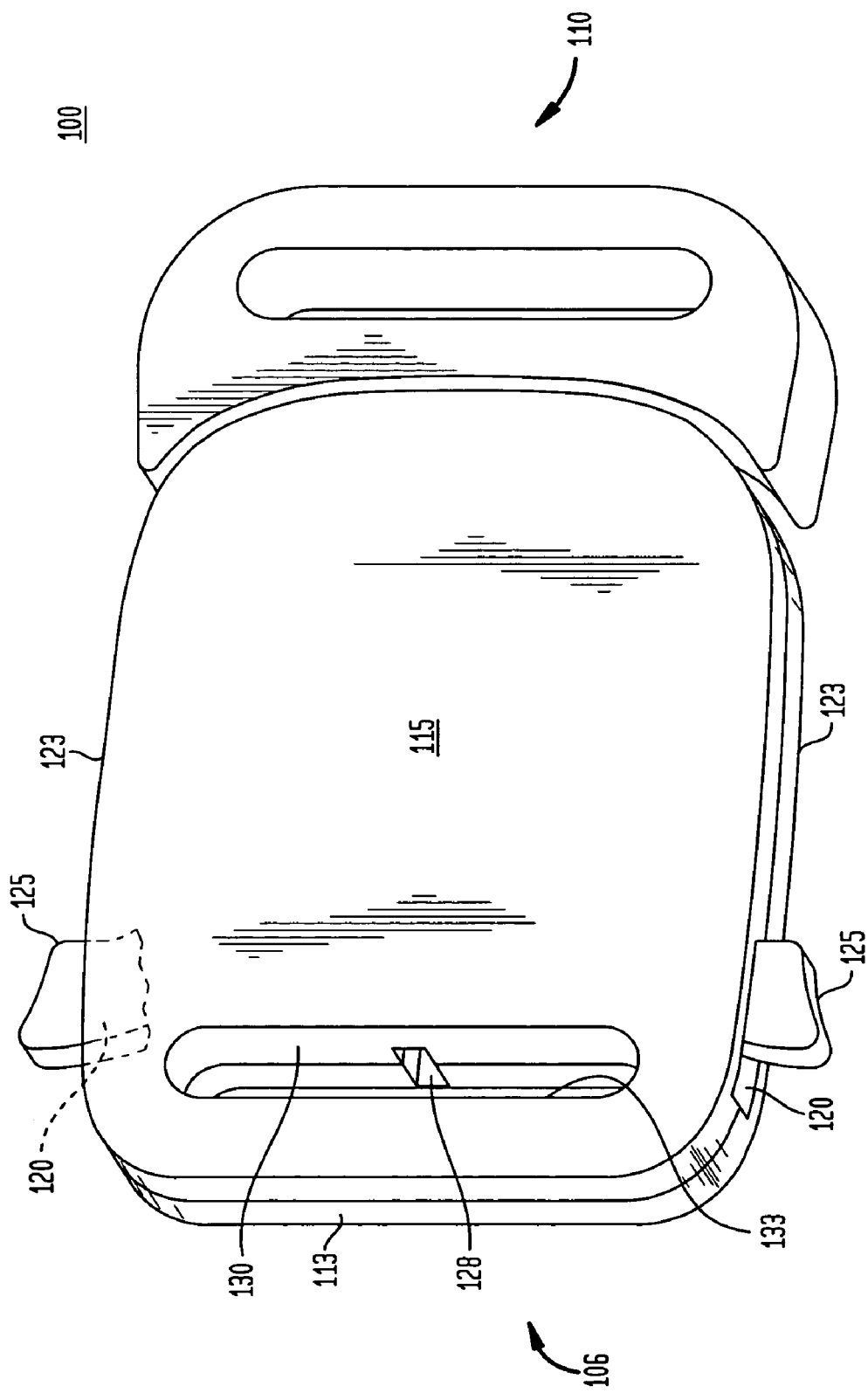

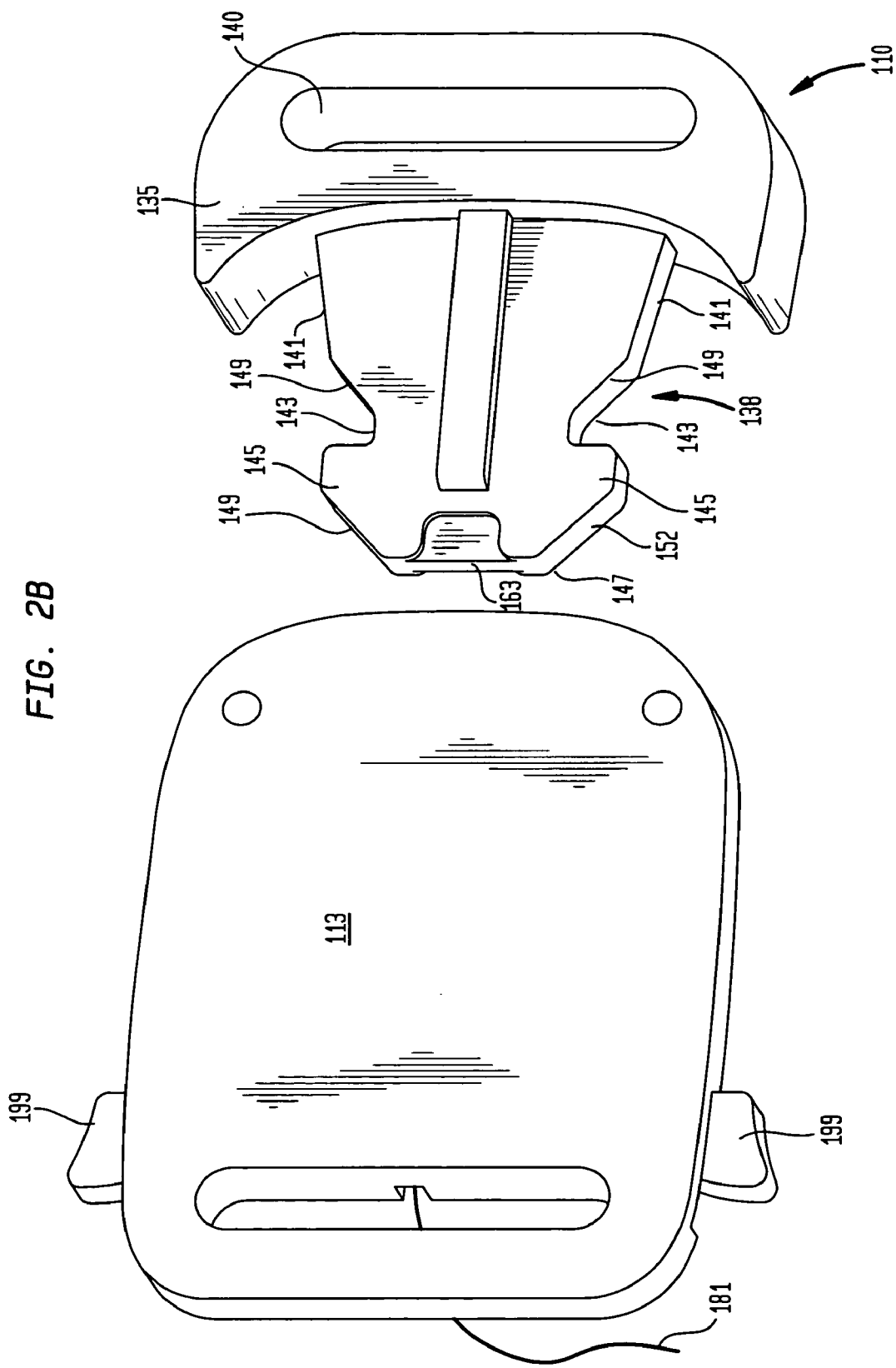

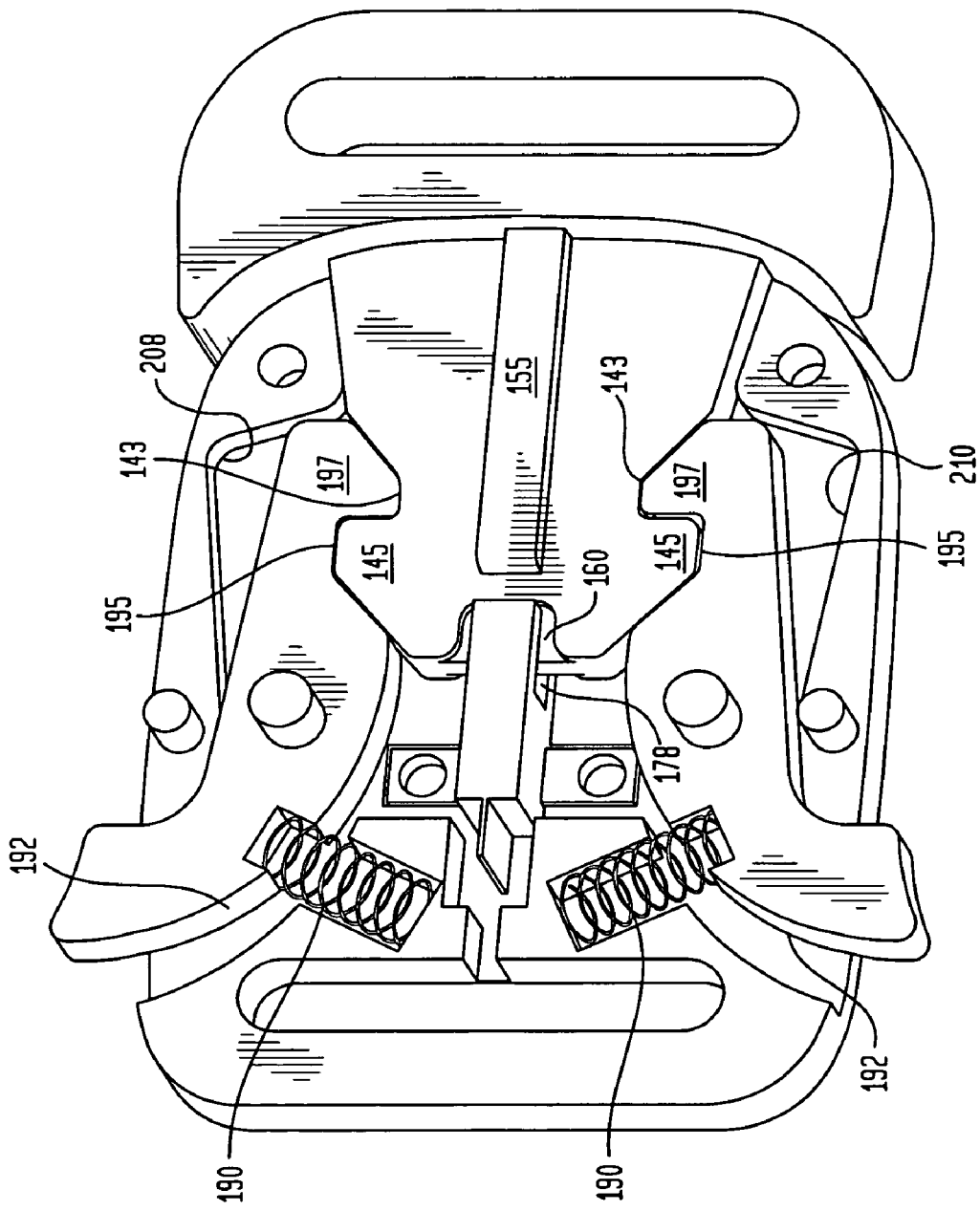

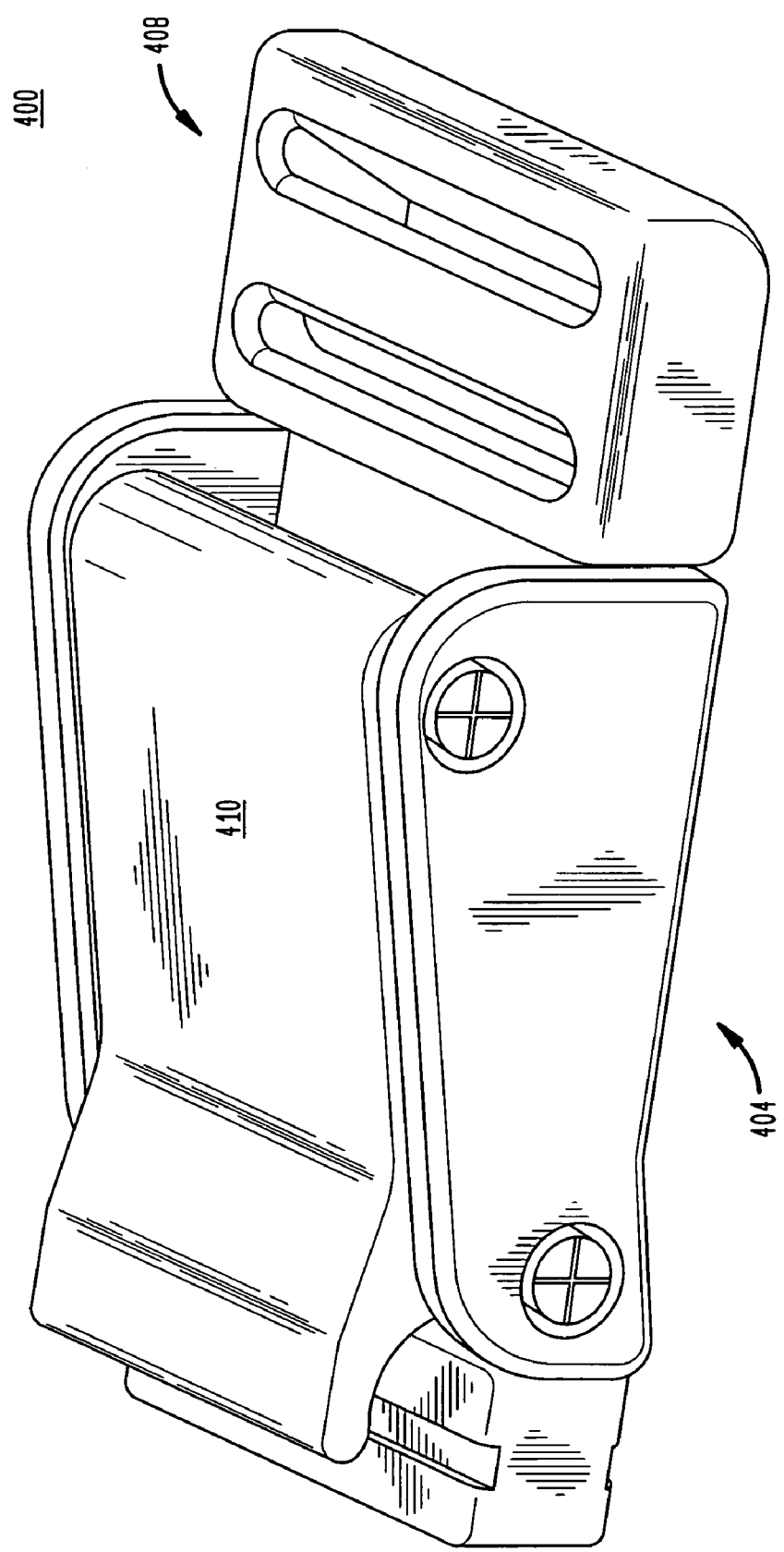

BELT BUCKLE AND USE THEREOF IN MAGNETIC RESONANCE IMAGING

BACKGROUND OF THE INVENTION

The present invention relates to magnetic resonance imaging systems, apparatus and procedures and, in particular, to apparatus and procedures for safely performing magnetic resonance imaging.

In magnetic resonance imaging, an object to be imaged as, for example, a body of a human subject, is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the precessing automatic nuclei to rotate or "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Many conventional magnetic resonance imaging instruments require that a patient lie on a horizontal bed that is then advanced into a tubular bore within a super-conducting solenoidal magnet used to generate the static magnetic field. Other conventional MRI imaging instruments use a magnet having a ferromagnetic frame defining a patient-receiving space. Considerable effort has been devoted to design of such magnets in a manner which provides a relatively open patient-receiving space, as opposed to the claustrophobic tubular bore of the conventional solenoidal magnet. However, in these instruments as well, it has been the common practice to provide the patient on a bed which remains horizontal throughout the procedure.

Advancement in magnetic resonance imaging has resulted in imaging apparatus that supports a patient in any position between a vertical position and a horizontal position. As described in greater detail in commonly assigned U.S. Pat. No. 6,414,490, which is a continuation of U.S. patent application Ser. No. 08/978,048, and U.S. patent application Ser. No. 09/718,946, the disclosures of which are hereby incorporated by reference herein, a magnetic resonance imaging system can be provided with a patient support, such as a table, which can extend in a generally vertical direction so that the long axis of the patient is substantially vertical. For example, the patient may be in a standing posture, with his back, side or front leaning against a generally vertical patient support. Such a support may include a footrest projecting from the table at its lower end and the patient may stand on the footrest. In other arrangements, the support includes a seat projecting from the table so that the seat is in a horizontal plane when the table surface is vertical. In particularly preferred arrangements, the patient support can move relative to the magnet. For example, the patient support may be arranged to move vertically relative to the magnet so as to elevate a portion of the patient into the patient-receiving space of the magnet. Alternatively or additionally, the patient support may be arranged to tilt through a range of orientations between a generally horizontal orientation and a generally vertical orientation.

Where a patient is positioned on the patient support and the patient support is adjusted to position the patient within the patient receiving space, the patient is often times strapped in place to prevent any unwanted movement and to prevent the patient from injury. Unwanted movement can extend the time it takes to acquire an imaging thereby reducing the throughput of the imaging apparatus. Where the patient is elderly or a child, straps of even greater import in preventing injury. Thus, in performing magnetic resonance imaging, it is often the case for an operator to strap a patient onto the patient support and operate any equipment ancillary to obtaining an image, e.g., computers, etc. After the patient is initially strapped, the operator nonetheless needs to be kept abreast of whether the patient has removed the straps or whether the buckle is properly latched during the imaging operation.

SUMMARY

An aspect of the present invention is the provision of a belt buckle assembly preferably comprising a housing including a base plate having a pair of longitudinal edges and a pair of lateral edges extending substantially transverse to the longitudinal edges. The housing further desirably includes a groove having an open end and a closed end centered between the longitudinal edges and extending parallel to the longitudinal edges. The housing also preferably includes at least one locking lever pivotally mounted along one of the longitudinal edges. The buckle assembly preferably also includes a locking member having a base portion, a tongue projecting from the base portion. The tongue desirably includes at least one planar surface, a lug projecting the planar surface, and a mating member mounted at an end opposite the locking member base portion. In an assembled position, the lug engages the groove and the tongue is secured by the locking lever.

Further in accordance with this aspect of the present invention, the open end of the groove forms an opening in one of the pair of lateral edges.

It is also desirable that the base plate includes a raised portion at the other end of the pair of lateral edges, the raised portion including at least one notch into which is mounted at least one spring, the spring exerting a force against each of said at least one locking lever.

In accordance with this aspect of the present invention, it may be preferable to have the at least one locking lever includes at least one notch that forms an ear and that the locking member includes longitudinal edges extending between the base portion and the end opposite the locking member base portion. Further still, at least one of the longitudinal ends of the tongue preferably includes a recess, such that in the assembled position, the notch engages the recess.

Further in accordance with this aspect of the present invention the assembly further comprises an optical switch member mounted on the base plate substantially adjacent the closed end of the groove. The optical switch may be coupled to a cable, preferably an optical or electrical cable.

The buckle assembly may further desirably include a handle portion for releasing said tongue, the handle portion protruding from a slot along one of the longitudinal edges.

Another aspect of the present invention is the provision of a belt buckle assembly that includes a locking member, a buckle housing for receiving the locking member, and an optical switch. In accordance with this aspect of the present invention, the optical switch is preferably disposed within the buckle housing and provides an indication of whether the locking member is secured to the buckle housing.

In accordance with this aspect of the present invention, the buckle housing includes a base plate having a pair of longitudinal edges, a pair of lateral edges extending substantially transverse to the longitudinal edges, and a groove having an open end and a closed end centered between the longitudinal edges and extending parallel to the longitudinal edges. The buckle housing further desirably includes a pair of locking levers each pivotally mounted along one of the longitudinal edges.

Further in accordance with this aspect of the present invention the base plate includes a raised portion at the other of the pair of lateral edges, the raised portion including a pair of notches into which are mounted a pair of springs, each of the springs exerting a force against each of the locking levers.

Further still, the locking member desirably includes a base portion, a tongue projecting from the base portion, the tongue having at least one planar surface, a lug protruding from the at least one planar surface and a mating member mounted at an end opposite the locking member base portion.

In yet another aspect of the present invention, a belt buckle assembly is provided. The belt buckle comprises a buckle housing including a base, first and second sidewalls projecting from said base so as to form a substantially U-shaped member, and a lug member that projects from the base. The belt buckle further desirably includes an electrical switch member having a pair of contact pins. The electrical switch member is fastened to the base. The buckle further desirably includes a tongue plate having a base portion and an elongated portion projecting from the base portion. The elongated portion includes a free end opposite the base portion. The tongue plate preferably includes a lower planar surface having a recess and a mating member mounted at its free end. In accordance with this aspect of the invention, the tongue plate is inserted in the housing such that the lug engages the recess and the mating member engages the contact pins.

In accordance with this aspect of the present invention the belt buckle preferably comprises a handle pivotally mounted onto to said sidewalls, the handle being operative to maintain the tongue plate in a locked position in said housing.

In accordance with this aspect of the present invention the mating member preferably comprises a portion that is gold plated for better conductivity. In addition, it may also be desirable to gold plate the contact pings.

Further in accordance with this aspect, it may be desirable to have the tongue plate include a bore.

It may be further desirable to provide belt buckle in accordance with this aspect of the present invention that is non-magnetic. Accordingly, such a belt buckle may be made from any number of non-magnetic materials including gall filled nylon, high strength ABS, high impact PVC or G-10 fiber glass resin. Any other non-magnetic material may be found also suitable.

In accordance with this aspect of the present invention it may be further desirable to include a moving platform member within the housing that maintains the tongue plate in a latch position.

Another aspect of the present invention is the provision of a belt buckle that comprises a non-magnetic housing having a switch member therein; and a non-magnetic locking member that is adapted to be received and secured by the housing, and wherein said switch member is capable of providing an indication that the locking member is secured by the housing. In accordance with this aspect of the present invention, the non-magnetic material may be selected from the class comprising glass filled nylon, high strength ABS, a G-10 fiberglass resin composite, or high impact PVC.

In accordance with this aspect of the present invention the belt buckle may form an assembly comprising a non-magnetic housing including a base plate having a pair of longitudinal edges and a pair of lateral edges extending substantially transverse to the longitudinal edges. The housing further desirably includes a groove having an open end and a closed end centered between the longitudinal edges and extending parallel to the longitudinal edges. The housing also preferably includes at least one locking lever pivotally mounted along one of the longitudinal edges. The buckle assembly preferably also includes a non-magnetic locking member having a base portion, a tongue projecting from the base portion. The tongue desirably includes at least one planar surface, a lug projecting the planar surface, and a mating member mounted at an end opposite the locking member base portion. In an assembled position, the lug engages the groove and the tongue is secured by the locking lever.

Alternatively, the belt buckle may preferably comprise a non-magnetic buckle housing including a base, first and second sidewalls projecting from said base so as to form a substantially U-shaped member, and a lug member that projects from the base. The belt buckle further desirably includes an electrical switch member having a pair of contact pins. The electrical switch member is fastened to the base. The buckle further desirably includes a non-magnetic tongue plate having a base portion and an elongated portion projecting from the base portion. The elongated portion includes a free end opposite the base portion. The tongue plate preferably includes a lower planar surface having a recess and a mating member mounted at its free end. In accordance with this aspect of the invention, the tongue plate is inserted in the housing such that the lug engages the recess and the mating member engages the contact pins.

Another aspect of the present invention is a combination for magnetic resonance imaging. The combination preferably includes a magnetic resonance imaging apparatus having a pair of opposed elements placed apart along a horizontal pole axis and defining a patient receiving space there between. The combination further includes a patient support positionable in the patient receiving space and a belt buckle assembly that includes a housing, a locking member and a switch member disposed within the housing.

Further in accordance with this latter aspect of the present invention the belt buckle assembly may comprise a non-magnetic housing including a base plate having a pair of longitudinal edges and a pair of lateral edges extending substantially transverse to the longitudinal edges. The housing further desirably includes a groove having an open end and a closed end centered between the longitudinal edges and extending parallel to the longitudinal edges. The housing also preferably includes at least one locking lever pivotally mounted along one of the longitudinal edges. The buckle assembly preferably also includes a non-magnetic locking member having a base portion, a tongue projecting from the base portion. The tongue desirably includes at least one planar surface, a lug projecting the planar surface, and a mating member mounted at an end opposite the locking member base portion. In an assembled position, the lug engages the groove and the tongue is secured by the locking lever.

It may be desirable in accordance with this latter aspect to also provide a belt buckle assembly comprising a non-magnetic buckle housing including a base, first and second sidewalls projecting from said base so as to form a substantially U-shaped member, and a lug member that projects from the base. The belt buckle further desirably includes an electrical switch member having a pair of contact pins. The electrical switch member is fastened to the base. The buckle further desirably includes a non-magnetic tongue plate having a base portion and an elongated portion projecting from the base portion. The elongated portion includes a free end opposite the base portion. The tongue plate preferably includes a lower planar surface having a recess and a mating member mounted at its free end. In accordance with this aspect of the invention, the tongue plate is inserted in the housing such that the lug engages the recess and the mating member engages the contact pins.

BRIEF DESCRIPTION OF THE DRAWINGS

FIG. 1 is a perspective view of a belt buckle assembly in accordance with an aspect of the present invention.

FIG. 2B illustratively depicts a bottom perspective view of the belt buckle assembly of FIG. 2A FIG. 3 illustrates the belt buckle assembly of FIG. 1 in a locked position.

FIG. 4 is a perspective view of a belt buckle assembly in accordance with another aspect of the present invention.

DETAILED DESCRIPTION

Figure 2A:
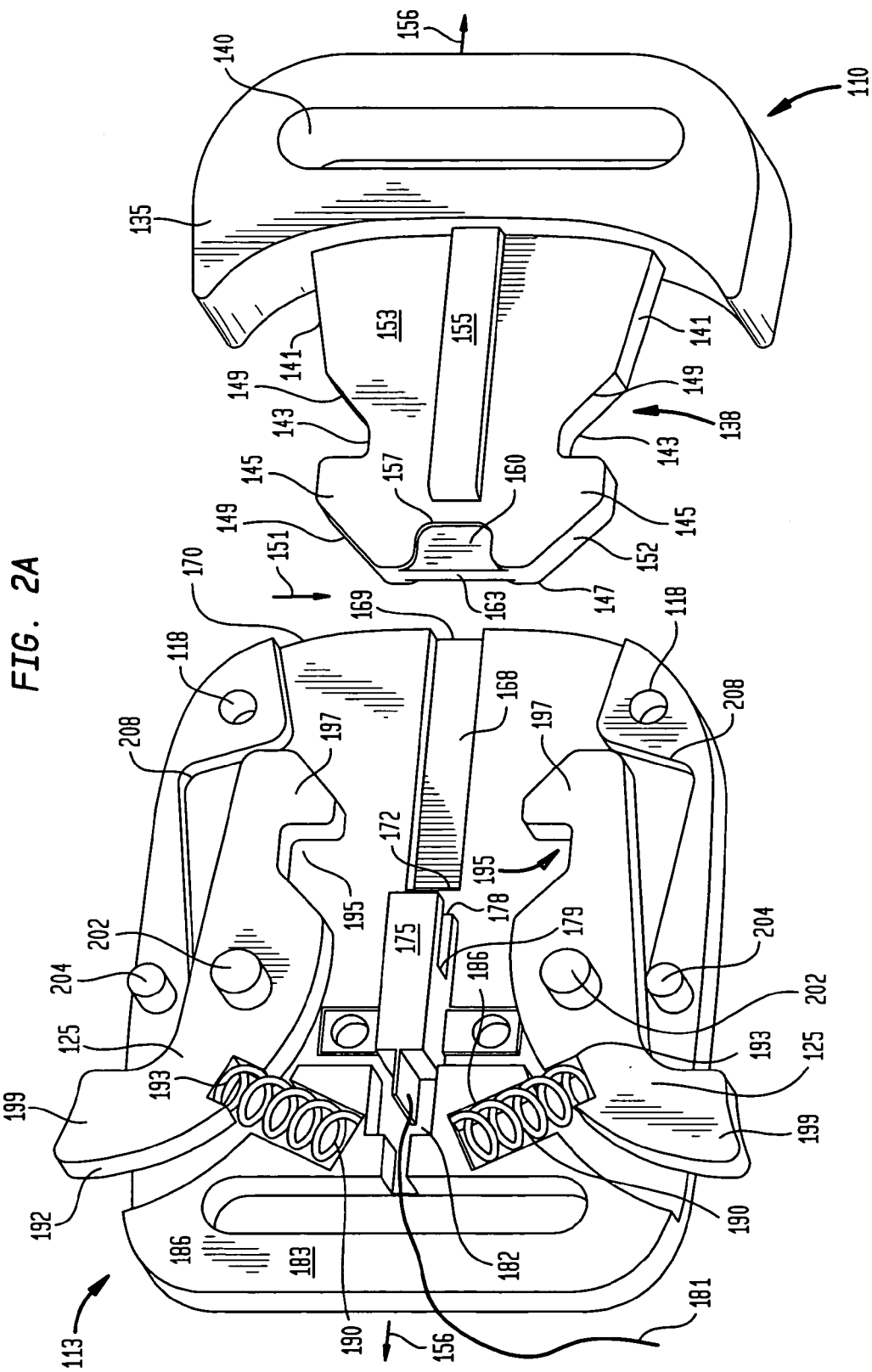
FIG. 2A illustratively depicts a top perspective view of the belt buckle assembly of FIG. 1 in an unlocked position with the top plate removed.

FIG. 1 shows a belt buckle assembly 100 in accordance with an aspect of the present invention. The belt buckle assembly 100 includes a housing 106 and a buckle clip or locking member 110. The housing includes a base plate 113 and a top plate 115. As is best seen in FIG. 2, the base plate 113 and top plate 115 are preferably connected together at apertures 118 using any number of fasteners including screws, rivets, lugs, keys, pins, etc. The base plate 113 and top plate 115 are machined so that when they are connected together openings 120 (see FIG. 1) are formed rearward on longitudinal sidewalls 123. The openings 120 provide passageways through which locking levers 125 are made accessible. The base plate 113 and top plate 115 are also machined so that when mated a second opening 128 is formed on the inner sidewalls 130 of a slot 133. The slot 133 is used to attach a belt webbing (not shown) to the housing 106 of the buckle assembly 100. The opening 128 provides a passageway through which any wires or cables (see FIG. 2) included in the housing may be threaded.

The belt buckle assembly 100 preferably comprises machined parts made from a G-10 fiberglass resin composite or high impact PVC, most preferably Type II high impact PVC. The belt buckle assembly 100 may also be made from any other magnetically translucent (i.e., non-magnetic) material that is able to reliably hold a patient in place without interfering with the magnetic field necessary to perform magnetic resonance imaging.

As best seen in FIG. 2A, the locking member 110 includes a base 135 and a tongue 138, which is secured to the base 135. The base 135 includes a slot 140 for attaching a belt webbing (not shown). The tongue 138 includes a pair of sidewalls 141 that extend in a longitudinal direction. A notch 143 is formed in each sidewall 141 so as to form an ear 145 relatively near a free end 147 of the tongue. In a preferred embodiment, the notches 143, 143 include a substantially L-shaped portion that terminates at one end into a sloped portion 149, 149 of the sidewalls 141. The sidewalls 141 continue from the sloped portions 149 toward the base 135. As shown, in the preferred embodiment the width (along the lateral direction 151) of the tongue 138 is larger at the base 135 than at the free end 147. In addition, the tongue 138 includes an angled portion 152 from the ear 145 to the free end 147 so that the width at the free end 147 is less than the width as measured across the ears 145.

The tongue includes an upper planar surface 153 onto which is formed a step 155 at a width-wise mid portion. As shown, the step 155 is substantially rectangular in shape and extends from the base 135 towards the free end 147 of the tongue 138 in a longitudinal direction 156. As is explained in further detail below, the step 155 is used to guide the tongue as the tongue 138 is inserted in the housing 106.

As best seen in FIG. 2B, the tongue 138 includes a lower planar surface that is machined in a like fashion to the upper planar surface 153. In particular, the lower planar surface includes a step that is similar in shape and structure to the step 155 on the upper planar surface 153. It is also possible to machine the tongue 138 so that only one of the planar surfaces includes a step, such as step 155. In such an embodiment, the planar surface having the step would need to be oriented such that the step would mate with its receiving recess in the housing. In the preferred embodiment both surfaces of the tongue are machined so that the tongue enters the housing regardless of which surface ends being adjacent to base plate 113.

Returning to FIG. 2A, a slot 157 is formed at the free end 147 of the tongue 138. The slot 157 includes an open face on the free end 147 into which is formed a jumper member 160. As seen, the jumper member 160 is machined as an integral part of the tongue 138. The free end 163 of the jumper member 160 is machined so as to be aligned with the free end 147 to provide a substantially flat surface.

The base plate 113 of the housing 106 includes a recess 168 formed at a width-wise mid portion. The recess 168 is substantially rectangular in shape and includes an open end 169 on an internal lateral sidewall 170. The recess 168 extends along the base plate 113 in the longitudinal direction 156 to a stop 172. The recess 168 provides an opening into which a step 155 on the tongue 138 can be inserted. As previously discussed, it is preferably that the tongue includes a step, such as step 155, on each of its planar surfaces. This advantageously allows the tongue 138 to properly mate with the housing without the requirement that a particular planar surface must face downward. However, it is possible to include the step 155 on only one planar surface of the tongue, however, in such an embodiment the tongue (as shown in FIG. 2A) would have to rotate 180° about the longitudinal axis 156 so the step 155 engages the recess 168 as the tongue is inserted in the housing. Thus, in accordance with the preferred embodiment depicted in FIGS. 2A and 2B, there is no directional preference when it comes to inserting the tongue into the housing. In addition, although the step 155 and recess 168 are substantially rectangular in shape, other shapes will work equally well.

In accordance with an aspect of the present invention, an optical switch 175 is mounted onto the base plate 113. As shown, the switch 175 is mounted at approximately the widthwise midpoint along the lateral direction proximate the stop 172. The switch 175 comprises a rectangular block that includes a slot 178 which serves as a receiving recess for the jumper member 160. When the tongue is inserted in the housing, the jumper member 160 enters the slot 178 such the jumper member's free end 163 abuts or is substantially adjacent to the closed end 179 of the slot 178. When the free end 163 abuts the closed end 179 a closed circuit is formed and indication of the closed circuit condition is communicated over a cable 181. The cable 181 may be threaded through a passageway 182 that terminates into the slot 128 and preferably comprises an electrical wire or cable. The cable 181 may also comprise an optical cable. In a preferred embodiment, the closed circuit condition is created when the ray path of infrared light, which is normally transmitted from the top portion of the switch 175 through the slot 178 to the bottom portion of the switch 175, is broken by the jumper member 160 occupying the slot 178. When the jumper member 160 occupies the slot 178, a photodetector resident at the bottom of the switch 175 is unable to receive any light from an LED (light emitting diode) resident at the top portion of the switch 175. Although in the preferred embodiment, an infrared optical switch is used, other types of switches may also be used.

The base plate 113 also includes a raised portion 183. A pair of substantially rectangular slots 186 is formed in the raised portion 183. A spring member 190 is positioned within each slot so as to exert a force on the locking levers 125. The spring members are made from a magnetically translucent material such as copper, although any other type of non-magnetic material may be used. Each locking lever 125 includes an arcuate run 192 having a slot 193. The slots 193, 193 form an opening for receiving the springs 190. At one end the arcuate run 192 terminates at a second slot 195. The second slot 195 forms an ear portion 197 on the locking lever 125. At another other end the arcuate run 192 terminates on the handle portion 199 of the locking lever 125 which protrudes from the housing 106.

Each of the locking levers 125 is pivotally mounted to the base plate 113 by a fastener 202. In the preferred embodiment, the fasteners 202, 202 comprise a pin member, however, other fasteners that allow the locking levers 125, 125 to pivot may also be used. A pair of guide pins 204 is also mounted to the base plate 113 along the longitudinal sidewalls 123.

In operation, the tongue member is inserted into the slot such that the step 155 is aligned with the recess 168. As the tongue 138 enters the housing 106, each angled portion 149 pushes each ear 197 of each locking lever 125 outward towards the longitudinal edges 123 into a notch 208. As the ears 197, 197 pivot outward the springs 190 are compressed and the handle portion 199 partially recedes into the slots 120. With the ears 197, 197 displaced, the tongue member enters the housing such that the jumper member 160 enters the slot 178. As best seen in FIG. 3, the tongue 138 is maintained in a locked position when the lever ears 197 engage the tongue member slots 143 and the tongue member ears 145 engage the slots 195. The springs 190, 190 maintain the buckle assembly in a locked position by exerting a force against the locking lever 125 at slots 193.

The tongue member 138 may be released by depressing the locking lever 125 at the handle portions 199 such that the lever pivots about the fastener 202 coming to rest (at its maximal displacement) into the notch 208 and against the wall 210. In this position, the tongue member may be withdrawn from the housing.

Although the belt buckle assembly 100 functions well in reliably retaining a patient in a strapped-in position during imaging, some care has to be taken in choosing the optical switch that provides an indication of whether a buckle assembly is properly latched. In particular, some optical switches include leads made of steel. The inclusion of even a minute amount of steel in the belt buckle assembly will affect the imaging process. More particularly, under most circumstances the presence of even particles of magnetic material (such as steel) within the imaging volume will prevent the acquisition of appropriate images.

FIG. 4 depicts a belt buckle 400 in accordance with another aspect of the present invention. The belt buckle 400 includes a housing 404 and a locking member 408. As shown, a handle 410 is pivotally mounted to the housing 404 and, as described in further detail below, provides a mechanism for releasing the locking member 408 from the housing 404.

Figure 5A:
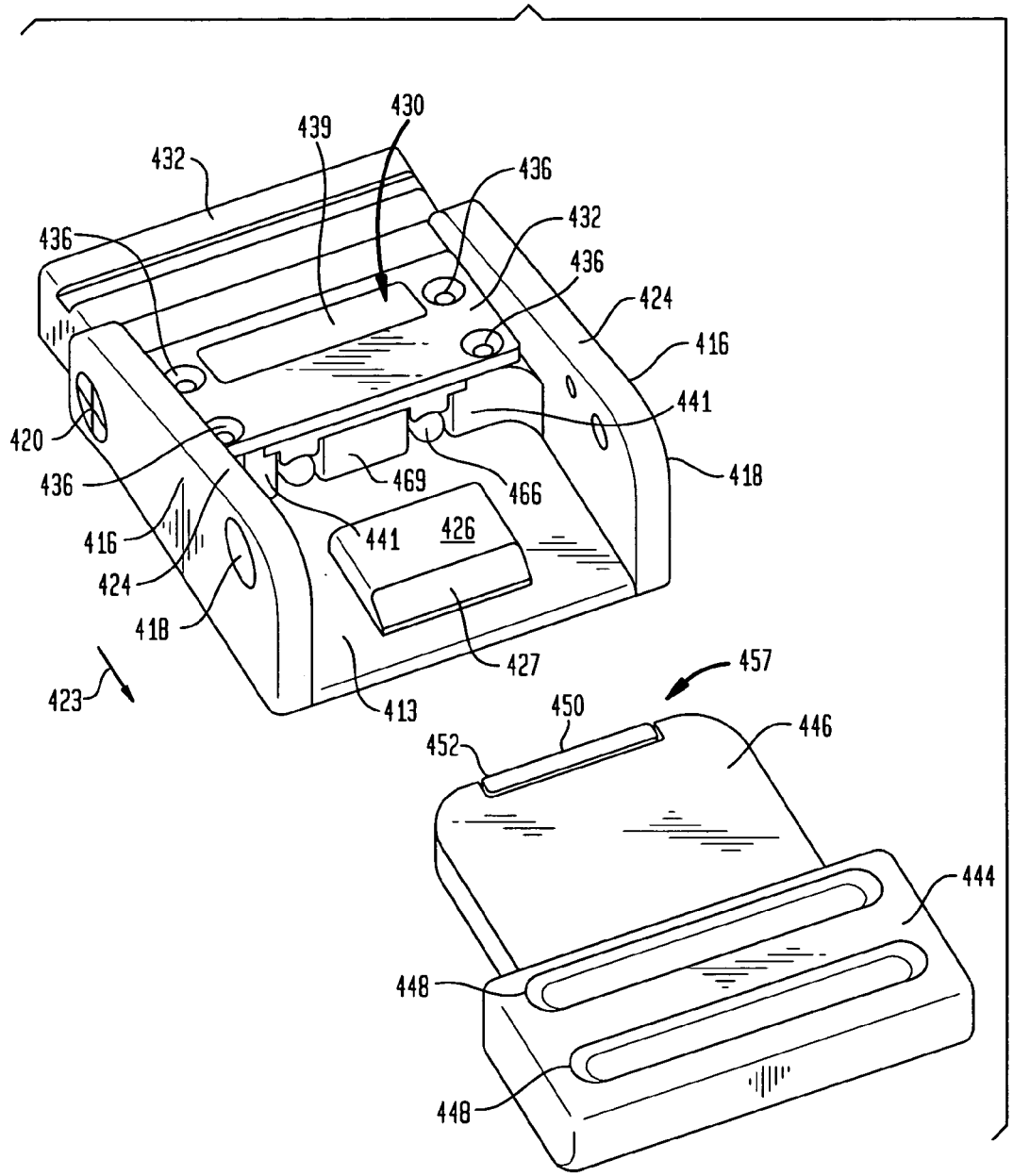
FIG. 5A illustrates the belt buckle assembly of FIG. 4 in an unlocked position.

As best seen in FIG. 5A, the housing 404 includes a base portion 413 and a pair of sidewalls 416, 416 that are formed substantially transverse to the surface of the base portion 413 at the edges thereof. Each sidewall 416 includes a pair of apertures 418 and 420. Aperture 418 is positioned at a front portion of the housing 404 and is used to pivotally mount the handle 410. Apertures 418 may be bored anywhere along sidewalls 418, as long as the geometry of motion of handle 410 is allowed. Aperture 420 is positioned towards the rear of the housing 404 and is used to mount a belt-receiving member 422. Any number of fasteners can be used to mount the handle 410 or belt receiving member 422 including a pin, a screw, a rivet, etc. This arrangement of the apertures 418 advantageously allows the handle 410 to have more clearance space within the housing during operation. This arrangement of the apertures 418 also advantageously allows a lug 426 formed onto the base 413 to project further away from the base 413, which allows the lug 426 to better engage the locking member 408. As shown, the lug 426 includes an angled face 427.

The housing 404 also includes an inner annular space 430 formed between base 413 and an upper plate member 432. The upper plate member 432 is substantially rectangular in shape and includes four mounting apertures 436 and a slot 439. The mounting apertures are used to secure the upper plate member 432 to the base 413. As shown (see FIG. 6), a mounting block 441 is formed adjacent to the sidewalls 416. The mounting block 441 preferably comprise a structure into which fasteners (not shown) may be threaded through the apertures 436 to secure the upper plate member 432 within the housing 404. Although the mounting block 441 is shown to comprise a unitary structure, it should be appreciated that the mounting block may comprise any design that provides the functionality as described herein. As is explained in further detail below, the slot 439 provides an opening for securing the handle 410 in the locked position.

The locking member 408 includes a base portion 444 and an elongated tongue member 446. The base portion 444 is substantially rectangular in shape and includes a pair of substantially rectangular slots 448. The slots 448 extend substantially transverse to the longitudinal direction 423 along the width of the base 444. The slots 448 serves as receiving recesses for a belt or strap that is secured to the base. The slots 448 also preferably allow for adjustment of any straps that are secured thereby.

Figure 5B:
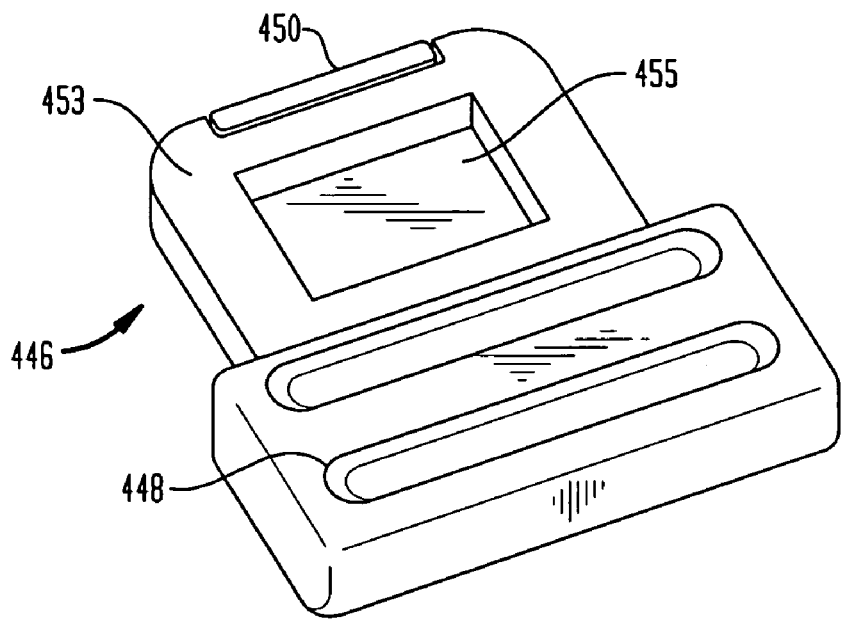
FIG. 5B depicts the lower surface of the locking member 408.
Figure 5C:
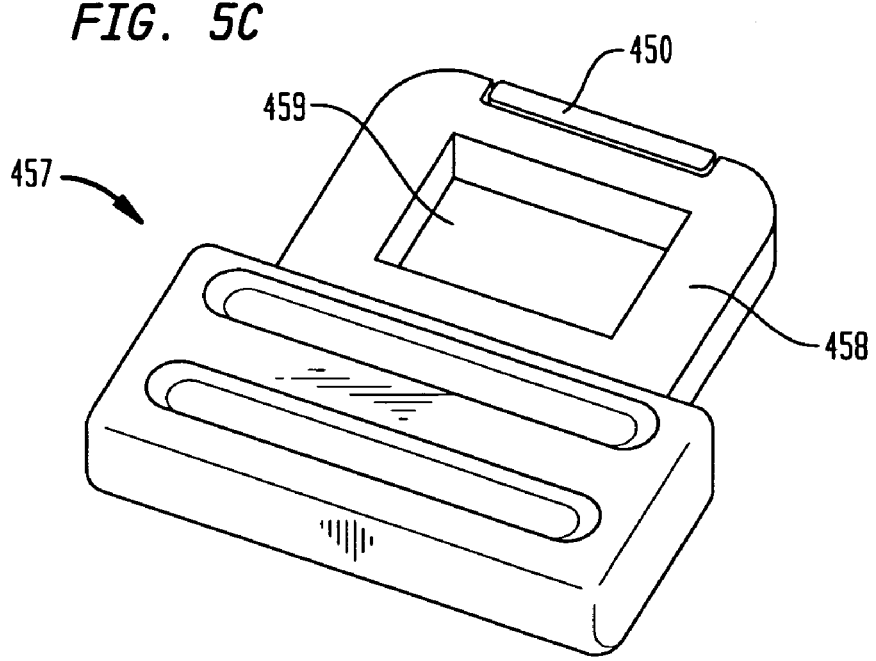
FIG. 5C depicts a locking member in accordance with a further aspect of the present invention.

The tongue member 446 is substantially rectangular in shape and includes a mate or jumper member 450 at its distal end 451. The mate member 450 is mounted within an opening 452 at the distal end of the tongue member 446. As best seen in FIG. 5B, the lower surface 453 of the tongue member 446 includes a well 455. As shown, the well 455 is substantially rectangular in shape to accept the lug 426. In addition to being rectangular in shape, the lug 426 and well 455 may also be square, circular or any other suitable shape. In addition, the tongue may include an aperture instead of a well for receiving the lug 426. In particular and as shown in FIG. 5C, a locking member 457 may include a tongue 458 having an aperture 459 that is secured by the lug 426. Aperture 459 is through hole that advantageously allows the lug 426 to secure the tongue 459 without any directional preference as to the orientation of the tongue or housing as the tongue enters the housing. In accordance with the embodiment shown in FIG. 5C, the locking member 458 may be inserted in the housing 404 without regard to a directional preference.

Figure 6:
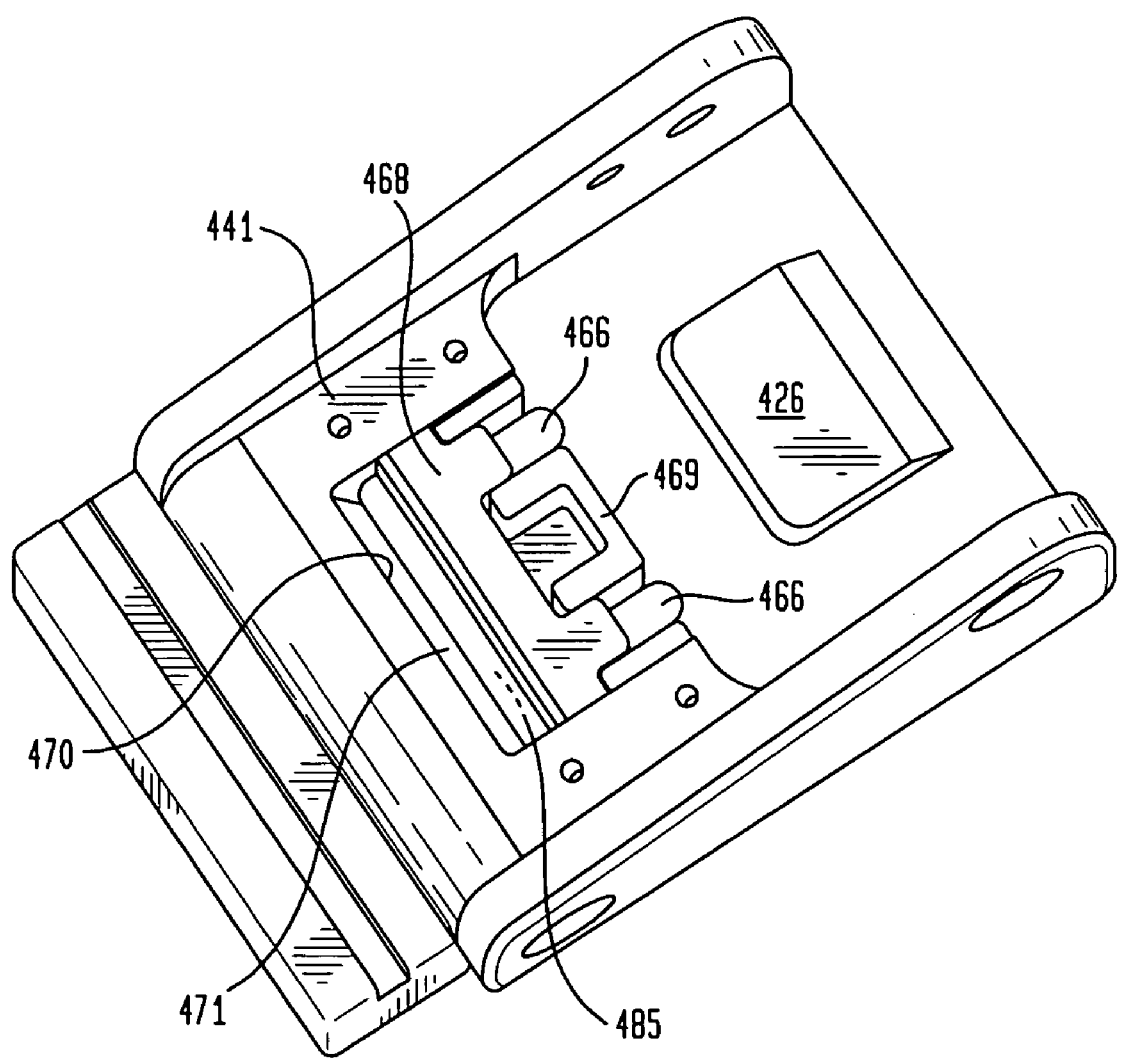
FIG. 6 illustrates the inner annular space of the housing belt buckle assembly of FIG. 4.

A pair of contact pins 466 are mounted within the annular space 430 to provide an indication of whether the belt buckle 400 is secure. As best seen in FIG. 6, the contact pins 466 are mounted into a contact pin holder 468. The contact pin holder 468 preferably includes a pair of pockets (not shown) for receiving the contact pins. The contact pins 466 are preferably spring loaded or mounted into the pin holder 468 and urge the contact pins 466 toward the lug 426. The pin holder 468 is mounted to the mounting block 441. A U-shaped member 469 is mounted to the base 413 and provides stop for the pin holder 468. The U-shaped member includes a pair of longitudinal sidewalls that extend parallel to the longitudinal direction and a lateral sidewall substantially transverse to the longitudinal sidewalls. The contact pins 466 may be made from any non-magnetic conductive material, such as copper, or may comprise any other non-magnetic material that is coated with a conductive material. The contact pin holder 468 acts as a moving platform in the latching operation of the buckle assembly. In particular, although for illustrative purposes, FIG. 6 shows a gap 471 between the pin holder 468 and the inner lateral sidewall 470 of the mounting block 441 when the assembly is unlatched, the pin holder 468 actually abuts the inner lateral sidewall 471. In addition, in this position, the contact pins 466 recede into the inner annular space 430 and may be arranged to recede partially or completely into the pin holder 468. As is explained in further detail below, the gap 471 provides an opening into which a portion of the flap is inserted when the assembly is in a latched or locked position.

Figure 7:
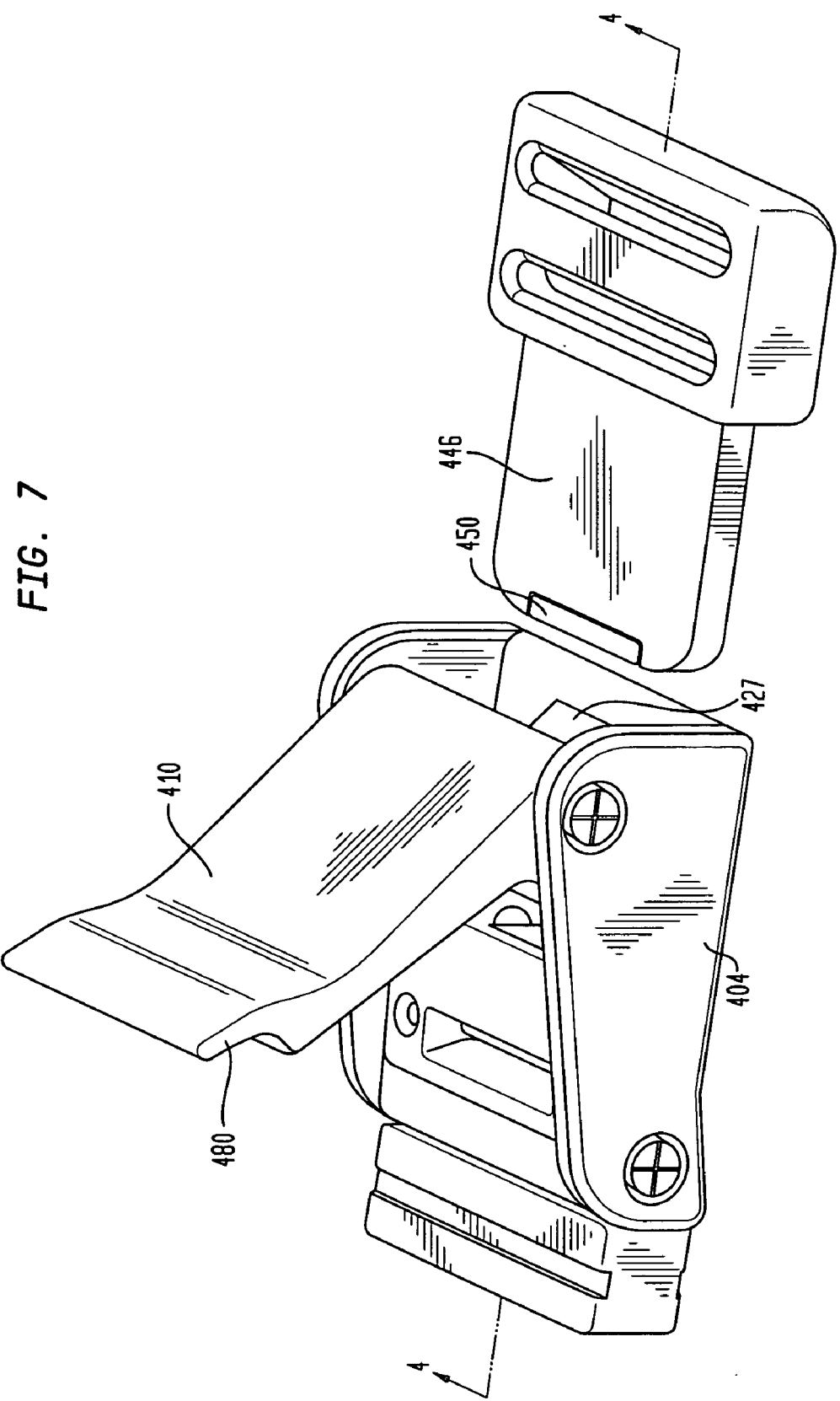
FIG. 7 illustrates another view of the belt buckle assembly of FIG. 4 in an unlocked position.

Turning now to FIG. 7, there is shown a perspective view of the belt buckle 400 with the handle 410 pivoted in the open position so that the locking member 408 may be inserted into the housing 404. As shown, a lip portion 480 is formed at the distal end of the handle 410. The lip portion is designed to provide access to the fingers. As the tongue member 446 is inserted in the housing 404 with the handle 410 pivoted in the open position, the tongue member 446 slides up and over the angled face 427 of the lug 426 and the well 455 (or aperture 459) envelops the lug 426. The handle 410 can be then returned to the locked position to secure the tongue member 446 and locking member 408 in the housing 404.

Figure 8:
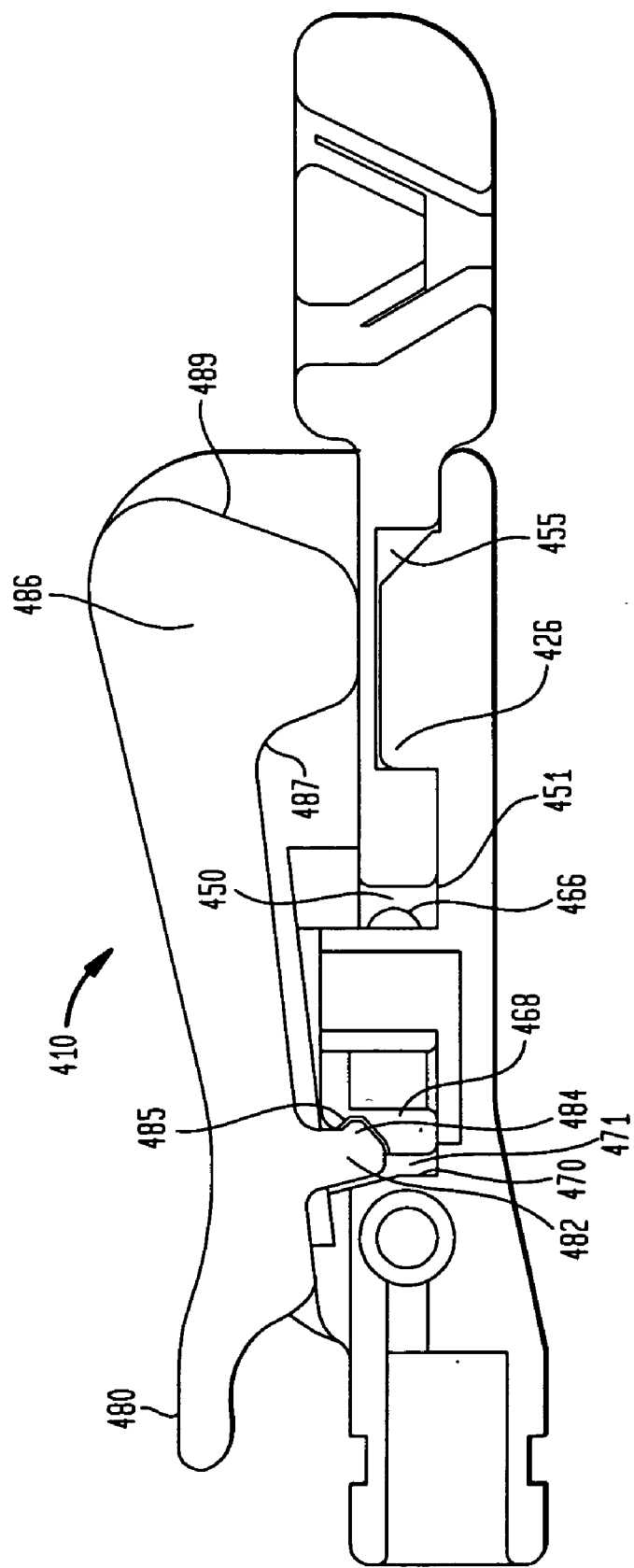
FIG. 8 is a side view along the 4—4 axis of the belt buckle assembly of FIG. 4 in a locked position.

As best seen in FIG. 8, the handle 410 also includes a protuberance 482. The protuberance 482 includes a lateral dimension that is slightly smaller than the lateral dimension of the gap 471. In addition, the protuberance 482 includes a protrusion 484. The protrusion 484 engages a notch 485 in the contact pin holder 468 in the latched position. The handle 410 also includes a head portion 486 at its proximal end. The head portion 486 includes a notch 487 and a face portion 489.

In the latched position, the handle 410 is folded into the housing 404 and the protuberance 482 forces the contact pin holder 468 forward and occupies the space created by the forward movement of the pin holder 468 in the longitudinal direction 156. The force applied by the handle 410 to the contact pin holder 468 causes the springs biasing the contact pins to compress, which, in turn, causes the pins 466 to move out of the inner annular space 430 and protrude beyond the lateral side of the U-shaped member 469. This causes the contact pin holder 468 to exert a return force against the handle 410. In addition, in the latched position the head portion 486 of the handle 410 is positioned so as to hold the tongue member in place. As shown, the well 455 (or aperture 459) envelops the lug 426 and the head portion 486 of the handle 410 assists in holding the tongue member 446 in place. The distal end 451 of the tongue member 446 also urges the contact pin members toward the handle 410 while the mating member 450 engages the stop member 469 and the contact pins. As shown in FIG. 8, the contact pins 466 may actually deform and enter the surface of the mating member 450. In addition, in the latched position, the protrusion 484 is hosted by the notch 485.

As the mating member 450 engages the contact pins 466 a closed circuit condition is caused. The closed circuit condition is then relayed to an indicator through electrical wires or other suitable means to a control console. In accordance with the buckle assembly 400, the mating member or jumper 450 forms a conductive path for an electrical signal between the contact pins 466. Thus, when the contact pins 466 touch the jumper 460 a closed loop or circuit is formed an electrical signal is received at an operator control. In a preferred embodiment the jumper is made of copper, which is gold plated to protect the jumper against corrosion. Likewise, the contact pins may comprise copper that is similarly gold plated. In general, however, any non-magnetic material that is a good electrical conductor may comprise either the contact pins or the jumper.

The buckle assembly 400 prepared via a molding process and is preferably made from glass-filled nylon or high-strength ABS. The strength of the buckle is proportional to the percentage of glass in the nylon. In an embodiment, we have found that 33% glass-filled nylon may be used to provide a belt buckle assembly of suitable strength. The use of magnetically translucent or non-magnetic materials in making the belt buckle assemblies in accordance with the present invention allows for a belt buckle assembly that is entirely non-magnetic and that may be used in any magnetic resonance imaging apparatus. We have found that molding provides a reduction in the costs of making the assemblies and provides additional flexibility with respect to geometry. In addition, molding allows for more complicated assemblies.

A variant in accordance with the present invention may include the provision of an optical switch, as discussed in relation to the assembly 100, in the assembly 400. Additionally, the electrical switch of the assembly 400 may be implemented in the assembly 100. It should also be noted that although the assembly 100 was machined, such an assembly may be prepared in accordance with a molding process. Other variants may include the use of a single locking lever in accordance with buckle assembly 100.

Figure 9:
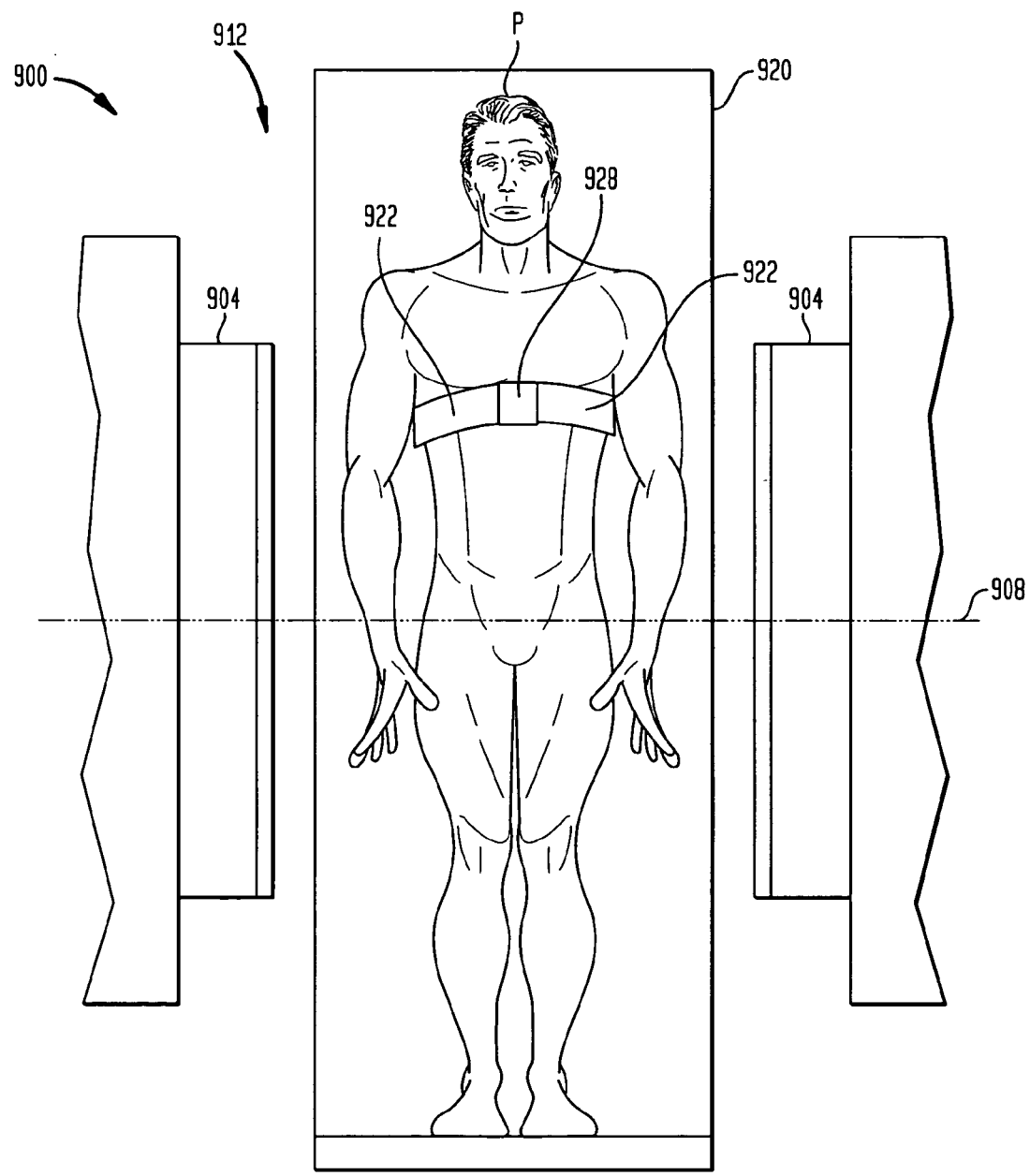
FIG. 9 illustratively depicts an embodiment of a magnetic resonance imaging apparatus in accordance with an aspect of the present invention.

Turning now to FIG. 9, there is illustrated a schematic of a magnetic resonance imaging apparatus in accordance with an aspect of the present invention. As shown, the apparatus 900 preferably includes a pair of opposed elements 904 spaced apart along a horizontal field axis 908. The space between the elements 904 is used as a patient receiving space 912. A patient support device 920 is positioned with the patient receiving space 912 and is used to support a patient P. The apparatus 900 is marketed and sold by Fonar Corporation of Long Island, N.Y. and various aspects of the apparatus are described in U.S. Pat. No. 6,414,490, and U.S. application Ser. Nos. 10/438,353, 10/427,443, and 10/301,187, all of which are assigned to the assignee of the present application and incorporated by reference herein in their entirety.

As shown, the patient P is standing in an upright position on the patient support device 920 and secured by a strap 922 and belt buckle assembly 928. Alternatively, the patient P may be seated and secured by a similar strap 922 and belt buckle arrangement 928. In accordance with the operational versatility of an apparatus such as apparatus 900, the patient may rotated about the horizontal axis between a fully upright vertical position, a horizontal position and even a reverse Trendelburg position. In addition, the patient may be raised or lowered. As the patient is positioned within the receiving space, it may be necessary to secure the patient to the support device to prevent injury. In accordance with an aspect of the present invention, either of the belt buckle assemblies 100 or 400, or any variant thereof may be used in conjunction with any number of straps or belts to secure the patient to the support. The optical or electrical latching detection circuit provided within the belt buckle assembly provides feedback to an operator or technician at a console, kiosk or podium (not shown) with an indication of whether the buckle assembly is secured or not. Typically, the console is located outside the shielded room, and the kiosk or podium is located in the shielded room with the apparatus. In conjunction with the positioning and imaging of the patient, where the buckle assembly provides an indication of an open circuit condition, the operation of the patient support 920 and/or the operation of the magnet (via elements 904) can be shut down or prevented. The indication or feedback may comprise audible or visual indication including, but not limited to, buzzers, lights or text. In contrast, where the belt buckle provides a closed circuit condition, the operator is free to safely position the patient and perform imaging.

In some circumstances, the feedback provided through the buckle assembly may be used to further indicate a patient that becomes disoriented or faints during the imaging process. This additional functionality may be implemented by use of a strain gauge in the webbings. These and other advantages of the present invention may be achieved not only in the apparatus depicted in FIG. 9, but in any imaging apparatus where patient safety is of consequence. Thus, the belt buckle assembly may be employed in an imaging apparatus where the patient is imaged entirely in the recumbent position in the bore of the magnet. As bore-type machines tend to be claustrophobic, the use of the belt buckle assemblies of the present invention may be used to provide an indication to an operator that the patient is buckled to the patient bed, and therefore it is safe to slide the bed into and out of the bore of such magnets.

Figure 10:
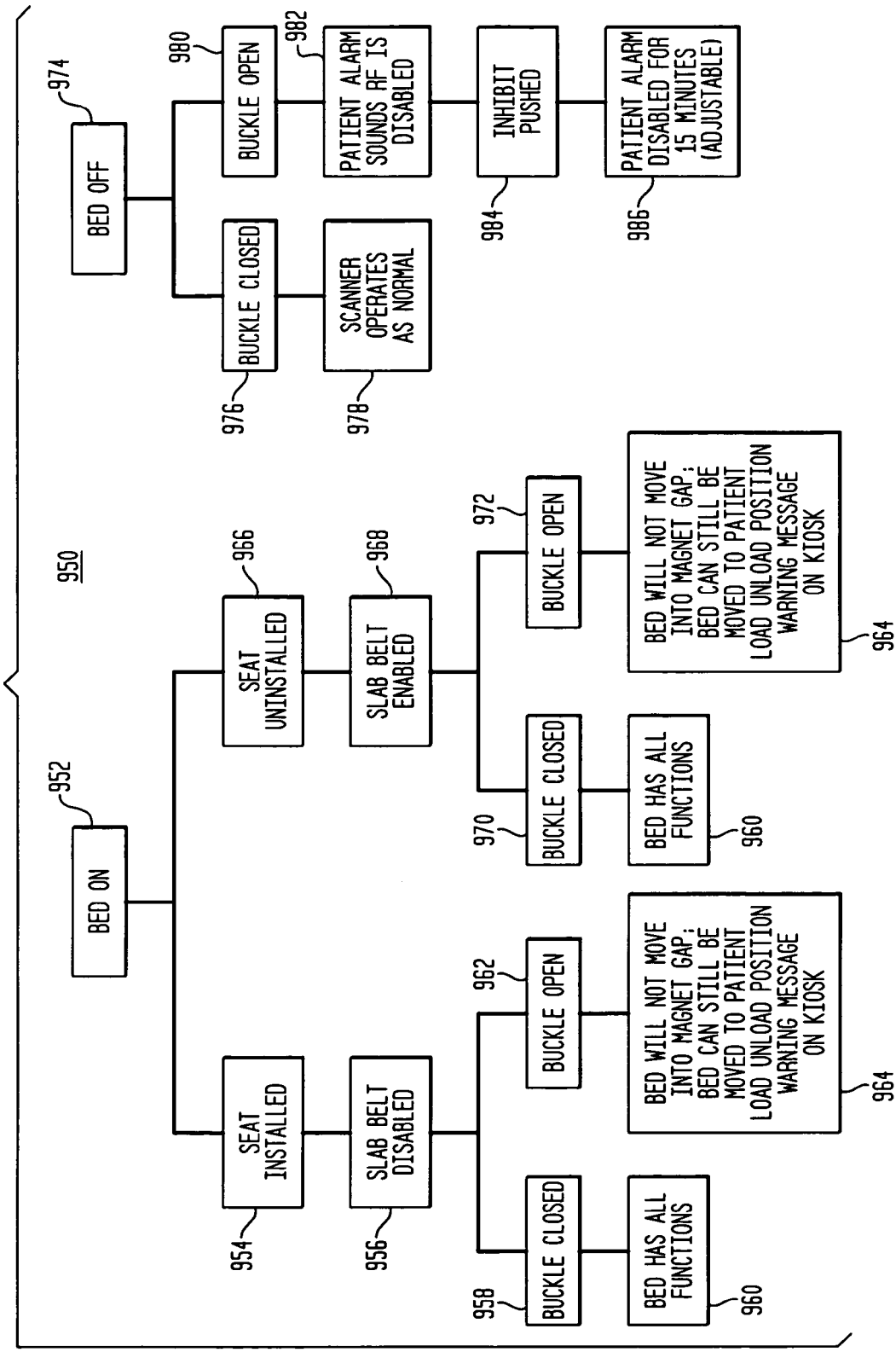
FIG. 10 depicts a schematic diagram of a switch in accordance with an aspect of the present invention.

FIG. 10 illustratively depicts an operational flow diagram 950 in accordance with an aspect of the present invention. In accordance with FIG. 10, the operation of the bed, e.g., patient support 920, and magnet may be controlled based on whether the buckle assembly is closed (e.g., latched) or opened (e.g., unlatched). As shown, if the bed is on (block 952) and a seat is installed (block 954), then the bed or slab belt is disabled (block 956). In this condition, if the buckle is closed (block 958), the bed has all its functions (block 960) and the position of the patient may be adjusted and imaging proceeds. If the buckle is open or not latched (block 962), the bed may be immobilized or its movement otherwise limited (block 964).

Where a seat is uninstalled (block 966), the slab belt is enabled (block 968). In this condition, if the buckle is closed (block 970), the bed has all its functions (block 960) as discussed above. If the buckle is open (block 972), the bed functions as shown and discussed in block 964.

Alternatively, the buckle assembly may also be configured to control the operation of the MRI apparatus, where the bed is off (block 974). When the bed is off (block 974) and the buckle is closed (block 976), the scanner operates as normal (block 978). In this embodiment, where the buckle is open (block 980), a patient alarm is activated (block 982) to notify an operator of such a condition. The system may be equipped with an inhibit control (block 984), which may disable the patient alarm for a predetermined amount of time (block 986) and which may be adjustable.

Figure 11A:
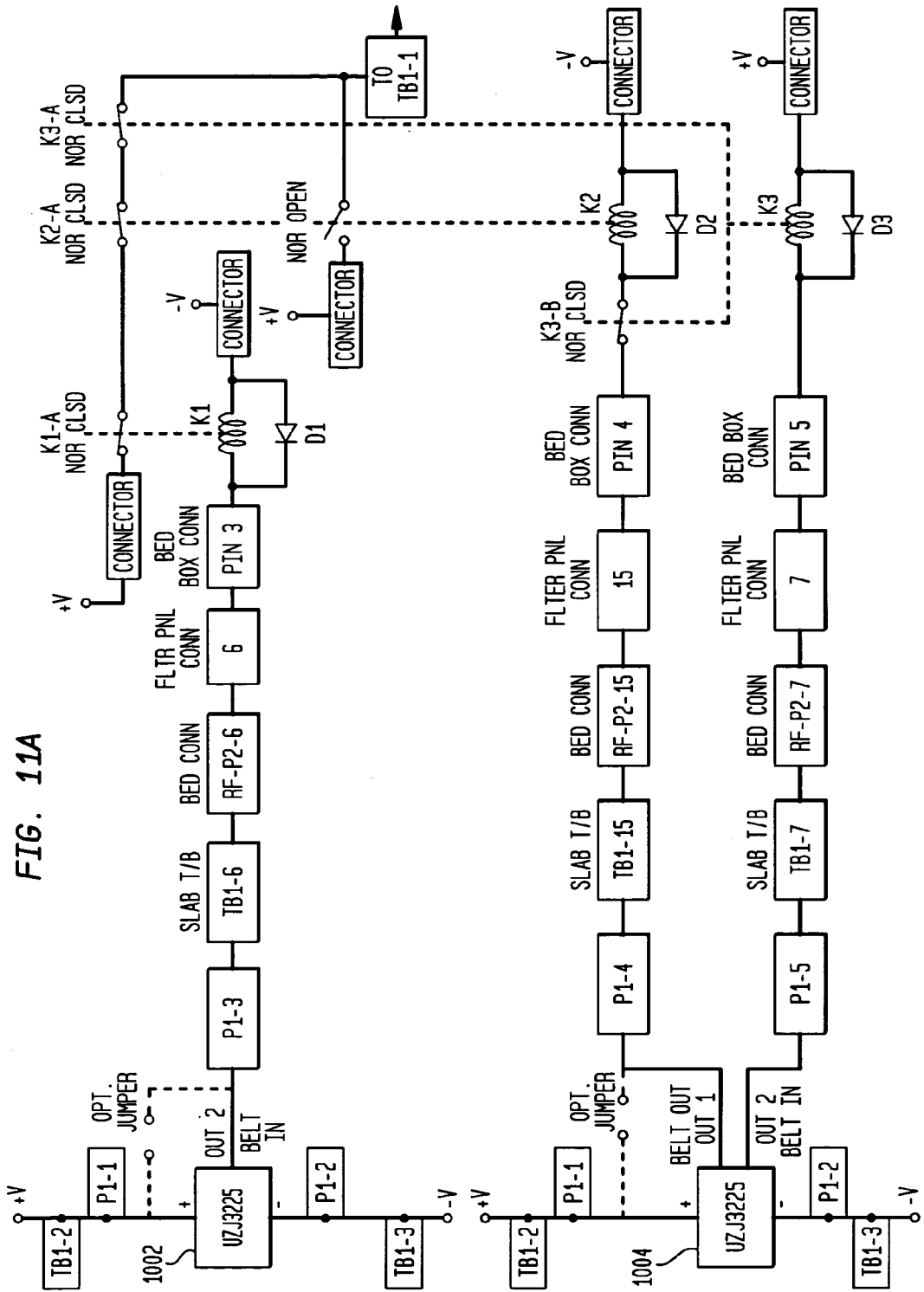
FIGS. 11A and 11B, when placed side-by-side, depict a schematic circuit diagram of a switch system illustrative of a further aspect of the present invention.
Figure 11B:
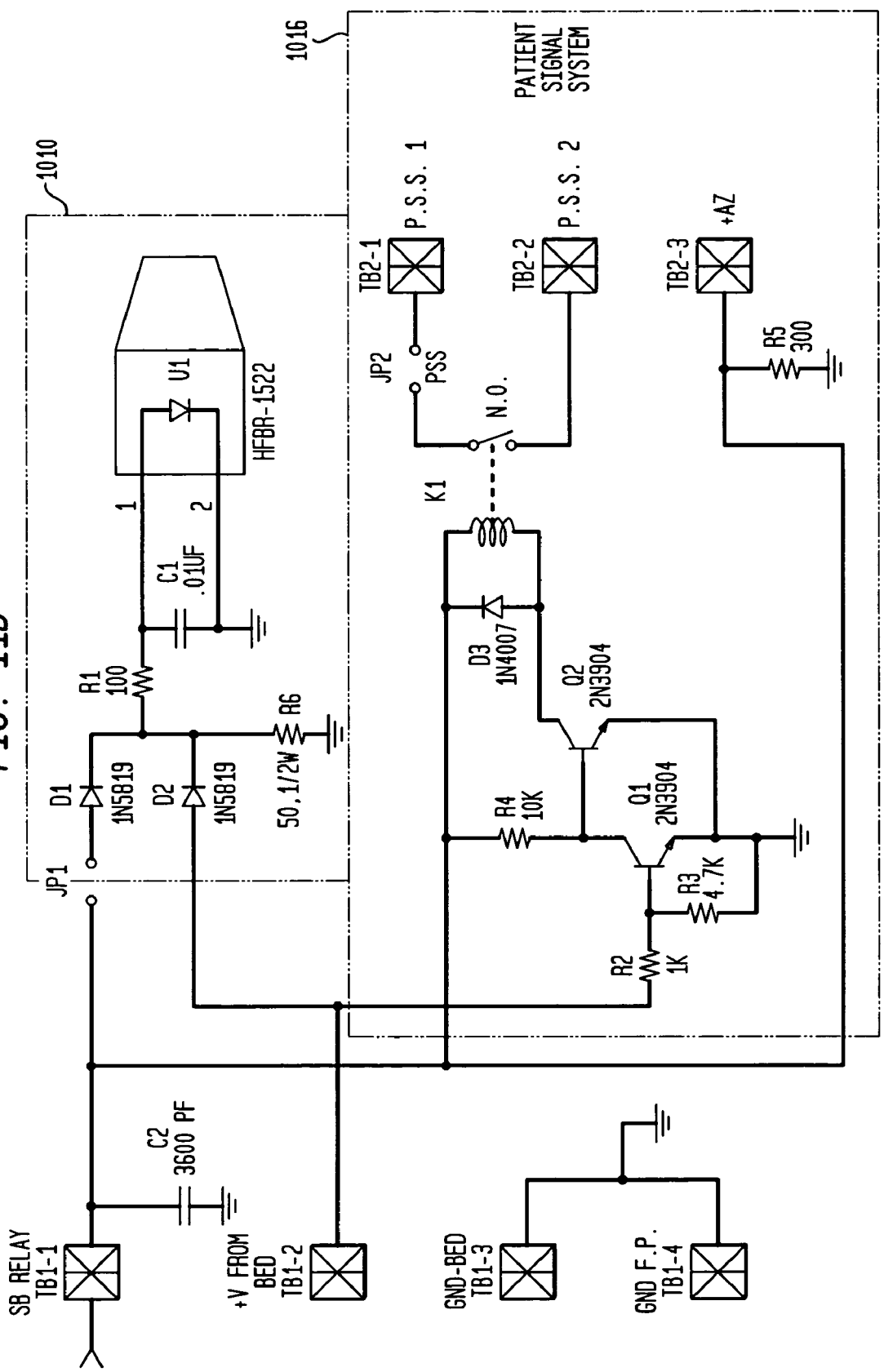

Turning now to FIGS. 11A and 11B, which, when placed side-by-side, comprise an illustrative schematic of switch circuit diagram that may be used in accordance with an aspect of the present invention. As shown, the outputs of a pair of optical switches 1002, 1004 are inductively coupled to a plurality of relay contacts. Although the a pair of optical switches 1002, 1004 are used in describing this aspect of the present invention, it is understood that the contact pins 466 and jumper 450 described herein above in relation belt buckle assembly 400 may be operated in a like manner. In operation, the switch 1004 comprises the switch on a buckle assembly for a seated patient, whereas switch 1002 comprises a buckle assembly for a patient standing upright (e.g., slab belt). The switch 1004 is arranged to bypass the need to detect the switch 1002 because if a patient is seated then the switch 1002 would not be used. An RF gate interrupt circuit 1010 is used to disable imaging whereas the circuitry 1016 is used to provide an indication of whether the buckle assembly is secured. When either of the switches 1002, 1004 detect the presence of the tongue within housing of the belt buckle assembly (100 or 400) a signal is provided to the block labeled bed connect ("bed conn") and bed box connect ("bed box conn") allowing the bed to be operationable. In addition, a signal is provided to TB1-1 which turns off the RF gate interrupt circuit thereby allowing the imaging process to proceed.

When the belt is unlatched, or no belt is present, and the bed control electronics is off, current from the closed contacts of K1-A on the system control assembly goes to the belt interlock PCB at terminal TB1-1. Current flows through diode D1 to fiber optic transmitter U1, and the lights and the internal LED (light emitting diode). Light is sent to another PCB in the system to prevent the RF power amp from gating on. Current from TB1-1 also flows through R4 and biases a transistor Q2 which turns on and energizes K1, a relay on the PCB, to sound an audible alarm that the buckle is unlatched. Current also flows to TB2-3, an output to the bed control electronics to prevent bed operation. If the slab belt buckle is properly latched, relay K1 on the system control assembly is energized and contacts K1-A open. RF transmitter operation is permitted. The resistor $R_5$ on the PCB holds the output TB2-3 to ground, which is recognized by the bed control electronics and permits bed motion.

If the seat assembly is installed, relay K2 is energized and contacts K-2A open. This isolates K1 from the circuit and makes the operation of the seat dominant. When the seat buckle is secured, relay K3 energizes. Contacts K3-B interrupt current flows to relay K2, which enables system operation, and contacts K3B open, which again isolates relay K1.

Referring to the PCB circuit, if the bed control electronics is on, current flows through diode D2 which lights fiber optic transmitter U1 to prevent RF operation. Current also flows through resistor R2 to bias Q1. This holds the base of Q2 to ground to prevent turn on of patient signal system K1. Resistor R3 holds the base of Q1 to ground to permit operation of Q2 when the bed control electronics is off. Resistor R6 and capacitors C1 and C2 are used to filter unwanted noise from false triggering of the RF gate interrupt.

The values of the circuit elements are for the particular embodiment shown; however, other values may be used to achieve this functionality.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A belt buckle, comprising:
   a non-magnetic housing including a base, first and second sidewalls projecting from said base so as to form a substantially U-shaped member and a lug member projecting from said base;
   an electrical switching member having a pair of contact pins, said switching member being fastened to said base; and
   a tongue plate having a base portion and an elongated portion projecting from said base portion, said elongated portion having a free-end opposite said base portion, a lower planar surface having a recess and mating member mounted at the free end thereof, and
   wherein in an assembled position said tongue plate is inserted in said non-magnetic housing such that said lug engages said recess and said mating member engages said contact pins.

2. The belt buckle of claim 1, further comprising a handle pivotally mounted onto to said sidewalls, said handle being operative to maintain said tongue plate in a locked position in said housing.

3. A combination for magnetic resonance imaging, comprising:
   a magnetic resonance imaging apparatus having a pair of opposed elements spaced apart along a horizontal pole axis and defining a patient receiving space therebetween;
   a patient support positionable in said patient receiving space; and
   a non-magnetic buckle assembly including a housing, a locking member and a switch member and wherein said switch member provides an indication that a patient is secured to said patient support.

4. The combination of claim 3, wherein said switch member comprises an optical switch.

5. The combination of claim 3, wherein said belt buckle assembly comprises an electrical switch.

6. A belt buckle, comprising:
   a non-magnetic housing having an inner annular space; and
   a switch member housed in the inner annular space; and
   a non-magnetic locking member that is adapted to be received and secured by said housing, and
   wherein said switch member is capable of providing an indication that the locking member is secured by said housing.

7. The belt buckle of claim 6 wherein said housing and locking member are made using materials comprising glass-filled nylon.

8. The belt buckle of claim 7 wherein said housing and locking member are made using materials comprising 33% glass nylon.

9. The belt buckle of claim 6 wherein said housing and locking member are made using materials comprising high-strength ABS.

10. The belt buckle of claim 6 wherein said housing and locking member are made using materials comprising G-10 fiberglass resin composite.

11. The belt buckle of claim 6 wherein said housing and locking member are made using materials comprising high-impact PVC.

12. The belt buckle of claim 6 wherein said switch member is an optical switch.

13. The belt buckle of claim 6, wherein said non-magnetic housing includes a base plate having a pair of longitudinal edges, a pair of lateral edges extending substantially transverse to said longitudinal edges, a groove having an open end and a closed end centered between said longitudinal edges and extending parallel to said longitudinal edges and a pair of locking levers each pivotally mounted along one of said longitudinal edges.

14. The belt buckle of claim 13, wherein said base plate includes a raised portion at the other of said pair of lateral edges, said raised portion including a pair of notches into which are mounted a pair of springs, each of said springs exerting a force against each of said locking levers.

15. The belt buckle of claim 13, wherein said non-magnetic locking member includes a base portion, a tongue projecting from said base portion, said tongue having at least one planar surface, a lug protruding from said at least one planar surface and a mating member mounted at an end opposite said non-magnetic locking member base portion.

16. The belt buckle of claim 15, wherein each of said locking levers include a notch that forms an ear and said non-magnetic locking member includes longitudinal edges extending between said base portion and said end opposite said non-magnetic locking member base portion, each of said longitudinal ends of said tongue including recesses, and wherein in said assembled position each of said notches engage one each of said recesses.

17. The belt buckle of claim 13, wherein said non-magnetic housing includes a base portion having a lug member projecting therefrom, a first sidewall and a second sidewall projecting from said base portion.

18. The belt buckle of claim 13, wherein said non-magnetic locking member includes a base portion and an elongated portion projecting from said base portion, said elongated portion including a free end opposite said base portion and a planar surface having a recess.

* * * * *